United States Patent [19]
Collier, IV et al.

[11] Patent Number: 5,702,377
[45] Date of Patent: Dec. 30, 1997

[54] WET LINER FOR CHILD TOILET TRAINING AID

[75] Inventors: Leslie Warren Collier, IV; Ali Yahiaoui; Eric Mitchell Johns, all of Roswell, Ga.; Debra Hartley Durrance, Appleton, Wis.

[73] Assignee: Kimberly-Clark Worldwide, Inc., Neenah, Wis.

[21] Appl. No.: 400,627

[22] Filed: Mar. 7, 1995

Related U.S. Application Data

[63] Continuation of Ser. No. 268,697, Sep. 1, 1994, abandoned.

[51] Int. Cl.⁶ .............................. A61F 13/15; A61F 13/20
[52] U.S. Cl. .................... 604/361; 604/378; 604/381; 604/385.1
[58] Field of Search .................... 604/361, 378, 604/385.1, 394–396, 381, 382; 128/885, 886

[56] References Cited

U.S. PATENT DOCUMENTS

| | | |
|---|---|---|
| Re. 32,026 | 11/1985 | Yamashita et al. . |
| 1,481,208 | 1/1924 | Johnson . |
| 2,261,473 | 11/1941 | Jennings . |
| 2,907,173 | 10/1959 | Robbins . |
| 3,175,558 | 3/1965 | Caillouette et al. . |
| 3,276,944 | 10/1966 | Levy . |
| 3,338,992 | 8/1967 | Kinney . |
| 3,341,394 | 9/1967 | Kinney . |
| 3,423,266 | 1/1969 | Davies et al. . |
| 3,502,538 | 3/1970 | Petersen . |
| 3,502,763 | 3/1970 | Hartmann . |
| 3,542,615 | 11/1970 | Dobo et al. . |
| 3,561,447 | 2/1971 | Alexander . |
| 3,613,687 | 10/1971 | Kennedy .................... 604/396 |
| 3,661,142 | 5/1972 | Flam . |
| 3,675,654 | 7/1972 | Baker et al. . |
| 3,692,618 | 9/1972 | Dorschner et al. . |
| 3,791,849 | 2/1974 | Hammer et al. . |
| 3,802,817 | 4/1974 | Matsuki et al. . |
| 3,809,096 | 5/1974 | York . |
| 3,838,692 | 10/1974 | Levesque . |
| 3,860,003 | 1/1975 | Buell . |
| 3,973,068 | 8/1976 | Weber . |
| 3,976,049 | 8/1976 | Yamashita et al. . |
| 3,977,202 | 8/1976 | Forusz et al. . |
| 3,980,070 | 9/1976 | Krupa . |
| 4,022,211 | 5/1977 | Timmons et al. . |
| 4,073,852 | 2/1978 | Mesek . |
| 4,081,256 | 3/1978 | Donnelly . |
| 4,092,454 | 5/1978 | Domoto et al. . |
| 4,106,001 | 8/1978 | Mahoney . |
| 4,240,416 | 12/1980 | Boich . |
| 4,295,517 | 10/1981 | Guex et al. . |

(List continued on next page.)

FOREIGN PATENT DOCUMENTS

| | | |
|---|---|---|
| 803714 | 1/1969 | Canada . |
| 2040602 | 10/1991 | Canada . |

(List continued on next page.)

OTHER PUBLICATIONS

ASTM D 1238–90b—Standard Test Method for Flow Rates of Thermoplastics by Extrusion Plastomer—pp. 272–275.
ASTM E 794–85 (Reapproved 1989)—Standard Test Method for Melting and Crystallization Temperatures by Thermal Analysis—pp. 584–586.

(List continued on next page.)

*Primary Examiner*—Mark Polutta
*Attorney, Agent, or Firm*—Patrick C. Wilson; Nicholas N. Leach; James B. Robinson

[57] ABSTRACT

Disclosed herein a personal care absorbent product which when first insulted, has a high initial surface moisture value which is maintained for several minutes but then, after a short period of time, drops to a lower value. As a result, the product has an initial "wet" feel but quickly changes to a drier feel so as to provide more comfort.

9 Claims, 2 Drawing Sheets

5,702,377
Page 2

U.S. PATENT DOCUMENTS

| Number | Date | Name | Ref |
|---|---|---|---|
| 4,302,853 | 12/1981 | Mesek . | |
| 4,340,563 | 7/1982 | Appel et al. . | |
| 4,419,403 | 12/1983 | Varona . | |
| 4,573,447 | 3/1986 | Thrash et al. . | |
| 4,615,695 | 10/1986 | Cooper . | |
| 4,639,390 | 1/1987 | Shoji . | |
| 4,639,949 | 2/1987 | Ales et al. . | |
| 4,640,284 | 2/1987 | Ruderian . | |
| 4,641,381 | 2/1987 | Heran et al. . | |
| 4,642,819 | 2/1987 | Ales et al. . | |
| 4,646,362 | 3/1987 | Heran et al. . | |
| 4,655,877 | 4/1987 | Horimoto et al. . | |
| 4,773,863 | 9/1988 | Douglas, III . | |
| 4,773,903 | 9/1988 | Weisman et al. . | |
| 4,786,530 | 11/1988 | Fox . | |
| 4,789,588 | 12/1988 | Suzuki et al. . | |
| 4,789,592 | 12/1988 | Taniguchi et al. . | |
| 4,794,002 | 12/1988 | Henis et al. . | |
| 4,854,332 | 8/1989 | Hanakura . | |
| 4,865,596 | 9/1989 | Weisman et al. . | |
| 4,885,204 | 12/1989 | Bither et al. . | |
| 4,888,238 | 12/1989 | Katz et al. . | |
| 4,923,454 | 5/1990 | Seymour et al. . | |
| 4,924,084 | 5/1990 | Lask et al. . | |
| 4,940,464 | 7/1990 | Van Gompel et al. . | |
| 4,960,414 | 10/1990 | Meyer | 604/394 |
| 4,987,908 | 1/1991 | Sprinkel et al. . | |
| 5,019,066 | 5/1991 | Freeland et al. . | |
| 5,026,364 | 6/1991 | Robertson . | |
| 5,043,704 | 8/1991 | Blakeney . | |
| 5,045,387 | 9/1991 | Schmalz . | |
| 5,062,839 | 11/1991 | Anderson | 604/396 |
| 5,074,854 | 12/1991 | Davis . | |
| 5,087,255 | 2/1992 | Sims . | |
| 5,102,668 | 4/1992 | Eichel et al. . | |
| 5,114,788 | 5/1992 | Nakagawa et al. . | |
| 5,120,598 | 6/1992 | Robeson et al. . | |
| 5,123,411 | 6/1992 | Noziri . | |
| 5,128,193 | 7/1992 | Anapol et al. . | |
| 5,130,073 | 7/1992 | Meirowitz et al. . | |
| 5,175,050 | 12/1992 | Meirowitz et al. . | |
| 5,178,139 | 1/1993 | Angelillo et al. . | |
| 5,192,606 | 3/1993 | Proxmire et al. . | |
| 5,197,958 | 3/1993 | Howell . | |
| 5,236,430 | 8/1993 | Bridges . | |
| 5,244,695 | 9/1993 | Davidowich et al. . | |
| 5,246,433 | 9/1993 | Hasse et al. . | |
| 5,254,399 | 10/1993 | Oku et al. . | |
| 5,264,269 | 11/1993 | Kakiuchi et al. . | |
| 5,291,617 | 3/1994 | Moretz et al. | 604/396 |
| 5,330,457 | 7/1994 | Cohen | 604/378 |
| 5,334,177 | 8/1994 | Cohen | 604/378 |
| 5,336,552 | 8/1994 | Strack et al. | 428/224 |
| 5,342,343 | 8/1994 | Kitaoka et al. | 604/385.2 |

FOREIGN PATENT DOCUMENTS

| Number | Date | Country | Ref |
|---|---|---|---|
| 1322940 | 10/1993 | Canada . | |
| 0320991A2 | 6/1989 | European Pat. Off. . | |
| 60-14960 | of 0000 | Japan . | |
| 1192871 | 8/1989 | Japan . | |
| 5059602 | 3/1993 | Japan | 604/385.2 |
| 2244201 | 11/1991 | United Kingdom . | |
| 2259018 | 3/1993 | United Kingdom . | |
| 86/04219 | 7/1986 | WIPO . | |
| 92/03113 | 3/1992 | WIPO . | |
| 93/09742 | 5/1993 | WIPO . | |
| 93/09746 | 5/1993 | WIPO . | |
| 93/17648 | 9/1993 | WIPO . | |
| 93/19716 | 10/1993 | WIPO . | |
| 93/24085 | 12/1993 | WIPO . | |
| 94/10958 | 5/1994 | WIPO . | |

OTHER PUBLICATIONS

ICI Surfactants Product Information Bulletin, ICI Americas Inc.

Material Safety Data Sheet for Developmental Products, ICI Americas Inc., 1991.

"The World of Surface Science" by D. O. Shah, University of Florida, Chemical Engineering Education, Winter 1977, pp. 14–23, and p. 48.

Dow Corning "Silicone Wetting Agents for Textile Applications" Fact Sheet, 1992 Dow Corning Corporation.

ICI Americas Inc. "Technical Bulletin for Ahcovel® Base N–62 Liquid Nonionic Textile Softener", Copyright 1978 ICI Americas, Inc.

ICI Rayca Technical Bulletin for Milease HPA, CA 706, Sep. 1990, ICI Americas Inc., Mt. Holly, N.C.

ICI Rayca Technical Bulletin for Milease T, CA 701, Sep. 1990, ICI Americas Inc., Mt. Holly, N.C.

ICI Rayca Milease® T. Finishing Agent Technical Sheet, Sep. 1989, ICI Specialty Chemicals, Wilmington, Delaware.

ICI Rayca "Quality Auxiliaries for the Textile Industry, A Guide to Selection", Sep. 1991, ICI Surfactants, Mt. Holly, N.C.

ICI Rayca "Textile Solutions ... Fiber to Fabric", Oct. 1991, ICI Surfactants, Mt. Holly, N.C.

ICI Surfactants—Catalogue of Surfactants and Derivatives, Ref. No. 50–3E/8167–191, Jun. 1993, published by ICI Europe Limited, Everslaan 45, B–3078, Everberg, Belgium.

PPG Industries, Inc., Material Safety Data Sheet, "Alubrasoft™77–N". Last revised Mar. 8, 1993.

PPG Industries, Inc., Material Safety Data Sheet, "Larosol ASR", Last revised Jan. 26, 1993.

PPG Industries, Inc., Material Safety Data Sheet, "Jordapon®CI Powder", Last revised Jul. 15, 1993.

PPG Textile Products Catalogue, Jun. 1991, PPG Industries, Inc. Gurnee, Illinois.

5,702,377

WET LINER FOR CHILD TOILET TRAINING AID

This application is a continuation of application Ser. No. 08/268,697 entitled "Wet Liner For Child Toilet Training Aid" and filed in the U.S. Patent and Trademark Office on Sep. 1, 1994, abandoned.

FIELD OF THE INVENTION

The present invention is directed to liner materials for personal care absorbent articles. More specifically, the present invention is directed to a fibrous nonwoven web liner material which has an initial wet feel to indicate to the user that an insult has occurred and then, with a passage of time, the liner material provides a drier and more comfortable feel.

BACKGROUND OF THE INVENTION

A major objective in the development of personal care absorbent products over the last decade has been the creation of liner materials which provide a clean and dry feel. Most personal care absorbent products including diapers, training pants, incontinence devices, sanitary napkins, bandages and the like employ a liner or body facing material which is adapted to be placed adjacent to the wearer's skin. Using diapers as an example, originally diapers were very wet to the touch once they had been insulted due to the inability of the diaper to channel fluids away from the wearer's skin to areas in the interior of the diaper where the liquid could be bound up and retained. As diaper and other personal care product designs have advanced, such products are increasingly more effective at channeling fluids away from the wearer's skin and thereby creating a much drier feel. This has a number of benefits including, but not limited to, skin wellness, especially with diaper rash, and improved comfort to the wearer.

In the area of diapers, one of the most recent advances has been the creation of training pants which are a cross or bridge between diapers and underwear for children. The purpose of the training pants is to provide a transitional garment during the toilet training stage of a child's development. It may be desirable if such devices as diapers, training pants and incontinence garments would initially, upon insult, feel wet or damp so as to alert the wearer and temporarily remind them of the fact that an insult has taken place. For a number of reasons, once the insult has taken place, it may not be practical or possible to change the soiled product. As a result, the wearer may have to wear the soiled product for some length of time. Consequently, once the initial signal of an accident has been given to the wearer, it would be desirable if the liner material would then revert to as dry a feeling as was possible so as to provide comfort to the wearer until such time as the product could be changed. There is therefore a need for a personal care absorbent article which has a liner material which will initially provide a "wet" feel to the wearer to indicate that an insult has taken place but which over time will provide the wearer with as dry a feel as is practically possible. The present invention is directed to such a liner material.

SUMMARY OF THE INVENTION

The present invention is directed to a personal care absorbent article with a wet liner which upon initial insult has a high relative surface moisture but then, within a short period of time, the relative surface moisture drops to a lower value so that long term the overall product should have a more comfortable feel. The personal care absorbent article includes a liquid permeable body side liner, an outer cover and an absorbent core disposed between the body side liner and the outer cover to form the article. The body side liner is made from a fibrous nonwoven web wherein the web includes a wetness indicator treatment which may comprise a mixture of sorbitan monooleate and polyethoxylated hydrogenated castor oil. It is desirable that the wetness indicator treatment be present on the web in an add-on of from 1 to 5 percent by weight based upon the total weight of the web. The resultant article has a relative surface moisture value of 60 percent or greater at approximately one minute after insult and a relative surface moisture value of 55 percent or less at approximately ten minutes. More preferably, the relative surface moisture value at one minute is 75 percent or greater.

In a more refined embodiment, the body side liner comprises a fibrous polyolefin nonwoven web having a basis weight ranging between about 0.5 and about 0.85 ounces per square yard. The outer cover may comprise a layer of polyolefin film attached to a layer of fibrous nonwoven web and the absorbent core may contain at least about 20 percent by weight superabsorbent based upon the total weight of the absorbent core. The personal care absorbent article of the present invention has a wide variety of applications including, but not limited to, use in the form of a training pant, diaper or incontinence garment.

DETAILED DESCRIPTION OF THE INVENTION

The present invention is directed to a personal care absorbent product with a wet liner for use as a child toilet training aid. The liner material of the present invention also can be used in other products and applications where a material is needed which when first insulted feels wet to the touch but, in a short period of time, again feels dry. Consequently, another use would be as a liner material for other personal care absorbent products including, but not limited to, diapers and incontinence garments.

Figure 1:
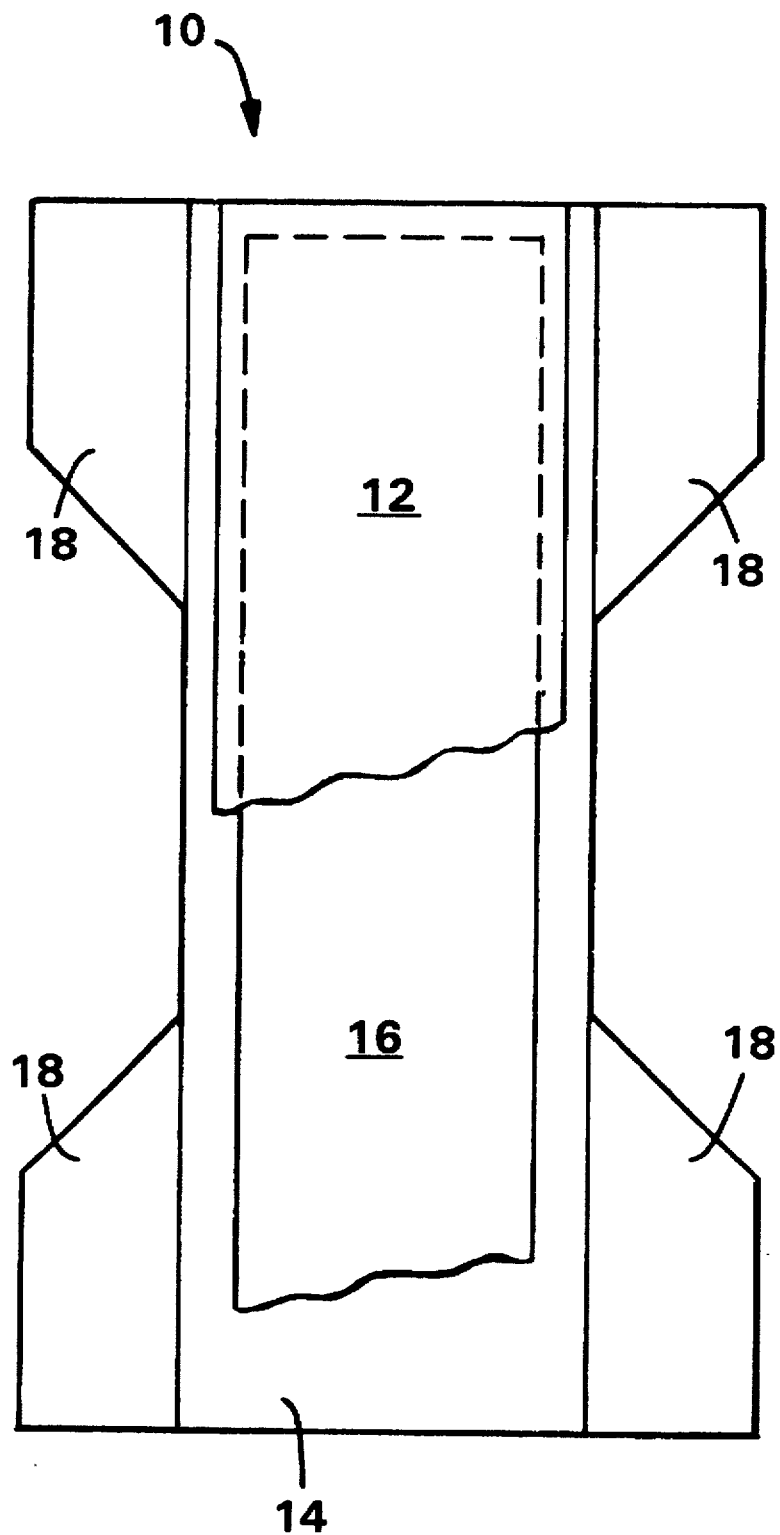
FIG. 1 is a partial cut-away top plan view of a personal care absorbent product, in this case, a training pant according to the present invention.

Personal care absorbent products include such items as diapers, training pants, sanitary napkins, incontinence garments, bandages and the like. Referring to FIG. 1, in their most basic design all such products 10 typically include a body side liner 12, an outer cover 14, and an absorbent core 16 disposed between the body side liner 12 and the outer core 14. Generally, the body side liner and the outer cover are sealed to one another about their peripheries so as to encapsulate the absorbent core and thus make it possible to entrap and retain any fluids contained within the absorbent core.

The wet body side liner 12 of the present invention comprises a web of material which is made from a plurality of fibers which are woven or nonwoven. Fibrous nonwoven webs have traditionally been found to work particularly well as the web material for the present invention. Examples of such webs includes, but are not limited to, spunbond webs, meltblown webs, bonded carded webs, air laid webs, wet laid webs, solution spun webs and generally any fibrous nonwoven web which has sufficient strength to be used as a liner for personal care absorbent products.

The fibers themselves can be any type of fiber, such as a short staple fiber or longer, more continuous fibers, as are found, for example, in meltblown and spunbond webs. The fibers can be natural or synthetic. Polyolefins, polyesters, cellulosics, polyacetates, and polyacrylate thermoplastics are some examples of polymers from which the fibers can be formed. In addition, it is possible to make fibers from homopolymers, copolymers, and blends of such polymers. It is also possible to form fibrous webs and/or blends of both synthetic fibers and natural fibers. Furthermore, the fibers may be hydrophilic or hydrophobic by nature or they may be treated to be such.

The fibers themselves may have a variety of cross-sectional constructions including, but not limited to, solid, hollow, round, or irregular shapes such as bilobal, trilobal, and "x-shaped." The fibers also may be multiconstituent fibers. For example, biconstituent and bicomponent fibers work particularly well for bonding the fibrous web together. This is because such fibers typically have a lower melting point component which is used for heat bonding and a higher melting component which adds strength and resiliency to the fibers. Generally, the fibers will have diameters which range between about 15 and 22 microns.

In order to provide sufficient in-use-strength, the fibrous web will most typically require additional bonding. Fibrous woven webs oftentimes have sufficient strength due to the weaving pattern used to form the web. Nonwoven webs, on the other hand, even with carding, have a relatively random fiber pattern or orientation. Consequently, such webs may require additional levels of fiber entanglement or bonding, collectively referred to as "bonding." Examples of bonding methods or techniques include, but are not limited to, hydroentangling, needling, stitching, heat bonding, adhesive bonding, and ultrasonic bonding. When the fibers forming all or a portion of the web are thermoplastic in nature, heat and ultrasonic bonding have been found to work particularly well. When bicomponent fibers are being used and/or a more lofty web is desired, through air bonding works well. When higher strengths are required, point bonding works well. Point bonding can be accomplished using, for example, ultrasonic bonding equipment or heated and patterned bonding rolls.

Once the web/liner has been formed, it is treated with a wetness indicator treatment which at least partially surrounds the exterior surfaces of the fibers to provide the web/liner with a wetness indicator. Conventional liner materials, such as surfactant treated polypropylene nonwoven webs, take in fluids very quickly and rapidly transfer the fluids to the underlying absorbent core. As a result, within a very short time, the liner feels dry to the user. By using a wetness indicator treatment, the relative surface moisture can be maintained at a higher level for a longer period of time. This is accomplished by way of the present invention. As is shown by the test data below, when plotting wetness versus time, current surfactant treated liners when wetted have an initial wetness, but this level of wetness drops off quickly with time. With the coating and liners of the present invention, higher wetness values are extended over a longer initial period of time while still having the liner ultimately return to an acceptable level of dryness in a reasonable period of time.

To accomplish the above-described effect, the fibers of the liner material are treated with a wetness indicator treatment comprising a mixture of sorbitan monooleate and polyethoxylated hydrogenated castor oil. Desirably, the coating is applied as an aqueous dispersion such that the treated portion of the liner has from about 1 to about 5 percent of the coating by weight, based upon the total weight of the treated portion of the liner. Such a coating material is available from ICI Americas Inc. of Wilmington, Del. and is designated Ahcovel® Base N-62 (G-1962) liquid nonionic textile softener. Ahcovel® Base N-62 is a concentrate which may be diluted to form fluid, high-solids aqueous dispersions. It is a blend of sorbitan monooleate (HLB of 4.3) and polyethoxylated hydrogenated caster oil (HLB of 10.8). Its specific gravity at 77° F. (25° C.) is approximately 1.10 and its viscosity at 25° C. is approximately 850 centipoise.

The outer cover of the present invention has the purpose of retaining any exudated body fluids or other liquids within the absorbent core of the personal care absorbent product. Plastic films and/or nonwovens and/or film/nonwoven laminates can be used to form the outer covers. Thermoplastic polymers including, but not limited to, polyolefins have been found to work particularly well as the forming material for both film and nonwoven outer covers. If desired, the outer cover may be made breathable through the use of breathable plastic films and/or through the use of aperturing.

The absorbent core which is disposed between the body side liner and the outer cover is used to absorb the main portion of the body fluids or other liquid delivered to it through the body side liner. Any of the currently available absorbent materials may be used to form the absorbent core. Examples of such materials include, but are not limited to, natural and synthetic wood pulp fluff fibers, hydrophilic thermoplastic fibers and superabsorbents.

Superabsorbents are water-swellable, water-soluble organic or inorganic materials capable, under the most favorable conditions, of absorbing at least about 20 times their weight and, more desirably, at least about 30 times their weight in an aqueous solution containing 0.9 weight percent sodium chloride. Organic materials suitable for use as superabsorbent materials in conjunction with the present invention can include natural materials such as agar, pectin, guar gum, and the like; as well as synthetic materials, such as synthetic hydrogel polymers. Such hydrogel polymers include, for example, alkali metal salts of polyacrylic acids, polyacrylamides, polyvinyl alcohol, ethylene maleic anhydride copolymers, polyvinyl ethers, methyl cellulose, carboxymethyl cellulose, hydroxypropylcellulose; and polymers and copolymers of vinyl sulfonic acid, polyacrylates, polyacrylamides, polyvinylpyrrolidone, and the like. Other suitable polymers include hydrolyzed acrylonitrile grafted starch, acrylic acid grafted starch, and isobutylene maleic anhydride polymers and mixtures thereof. The hydrogel polymers are preferably lightly crosslinked to render the materials substantially water insoluble. Crosslinking may, for example, be accomplished by irradiation or by covalent, ionic, van der Waals, or hydrogen bonding. The superabsorbent materials may be in any form suitable for use in absorbent composites including particles, fibers, flakes, spheres, and the like. Such superabsorbents are usually available in particle sizes ranging from about 20 to about 1000 microns. The absorbent core 16 can contain from 0 to 100 percent superabsorbent by weight based upon the total weight of the absorbent core.

Depending upon the design of the particular personal care absorbent product, other components also may be included. For example, referring again to FIG. 1, if the personal care absorbent product 10 is a training pant, it also may include elastic side panels 18. The product also may include (not shown) such things fluid containment flaps, fastening devices and other layers of liquid transfer or retention material.

Having thus described the invention in detail, several samples of the present invention were prepared and tested for their relative surface moisture in accordance with the test procedure set forth below.

TEST METHODS

Relative Surface Moisture Test

The relative surface moisture in the liner and overall product was calculated from measurements made using a Surface Dryness Measuring Equipment apparatus manufactured by Hoechst Atkiengesellschaft of West Germany. A detailed description of this type of equipment and its operation can be found in U.S. Pat. No. 4,924,084 to Lask et al. which is incorporated herein by reference in its entirety. The equipment for this apparatus included a Strip chart recorder from the Linear Instrument Corporation of Reno, Nev. (Model 1201). The chart recorder recorded moisture readings from an optical light sensor which in turn was connected to a DC power source. Prior to the conductance of testing, the equipment was turned on and allowed to warm up for a minimum of 45 minutes.

To test each sample, each sample was placed on top of a plexiglass plate approximately the same size as that of the sample. In order to normalize the moisture values for each sample, a dry reading and a wet reading were both obtained in addition to the actual wetness curve which was generated over a preselected time interval which in this case was 10 minutes.

To obtain a dry reading and thus a lower limit on the graph, the sensor was placed over the top of the sample with the longitudinal axis of the sensor being perpendicular to the longitudinal axis of the sample and with the ends of the optical light sensor extending equidistant over both side edges of the sample. The sample was positioned with the liner side adjacent the light sensor and the back sheet facing the plexiglass support. The chart pen was then activated by switching the recorder from stand-by to record and the pen was then zeroed over the 20 grid mark location and the recorder was then returned to stand-by and the detector was removed from the sample.

Next a stainless steel ring having a 6 centimeter inner diameter, a height of 4 centimeters and a weight of approximately 326 grams was centered over the longitudinal and transverse center of the sample in the same location as the dry reading was taken. Into the center of the steel ring there was poured 80 milliliters of certified blood bank saline (Catalogue No. B3158-1) from the Baxter Healthcare Corporation, Scientific Products Division, McGaw Park, Ill. The saline solution was a stabilized isotonic 0.9% saline solution containing no preservatives. The saline solution was at ambient temperature (72° to 74° F.) (22° to 23° C.). The 80 milliliters of saline solution was quickly poured into the ring and thus onto the liner side of the absorbent sample. Immediately after the saline solution was absorbed below the surface of the liner (no excess liquid standing on the liner), the stainless steel ring was removed and the optical light sensor was immediately placed on top of the sample in the same manner as described before and the chart recorder was switched from stand-by to record. The recorder was adjusted to a chart speed of 1 centimeter per minute and the test was allowed to run for a total of ten minutes. At the end of the ten minute interval, the chart pen was lifted and the chart was turned off by switching the chart to stand-by. Next, the ring was placed back on top of the sample in the same location as before and the sample was totally saturated by pouring an additional quantity of saline solution generally in an amount of about 100 milliliters so as to completely saturate the absorbent core. The amount of liquid in the pad after the second insult should be enough such that the weight of the sensor causes slight flow back of the liquid to the surface. The ring was then removed and the optical light sensor, whose optical sensing portion had been wiped free of any excess saline solution from the previous measurement, was placed in the same location on top of the sample in the same manner as described above. The chart was again switched from stand-by to record and the chart was either momentarily activated or the chart paper was moved back and forth so as to achieve a mark or location on the grid paper representing the total saturation measurement for the sample. Having done this, each sample then has a zero or dry value ($V_D$), a total saturation value ($V_S$) and a time dependent curve extending from the point of absorption of the initial 80 milliliters of saline solution to a point ten minutes later.

Following the collection of this data, the relative surface moisture values were calculated using the following equation:

$$\text{relative surface moisture } (\%) = \frac{V_T - V_D}{V_S - V_D} \times 100 = V_R$$

where:

$V_T$ is the value on the curve at a given time.

$V_D$ is the value on the curve when the sample is dry. $V_D$ equaled 20 for all examples tested.

$V_S$ is the value on the curve when the sample is saturated.

EXAMPLES

To demonstrate the present invention, a training pant was made according to the present invention and it was tested against a currently available Kimberly-Clark Huggies® Pull-ups® training pant (size 2) and a Procter and Gamble Pampers® Trainers® training pant for percent moisture at one and ten minutes using the test outlined above.

The Pampers® Trainers® training pant had a body side liner believed to contain rayon staple fibers, an absorbent core which contained superabsorbent, an outer cover and elastic side panels.

The currently available Kimberly-Clark Huggies® Pull-Ups® training pants had an outer cover including an interior layer of 0.7 mil (18 microns) thick polypropylene film adhesively laminated to an exterior layer of 0.8 ounce per square yard (27 grams per square meter (gsm)) polypropylene spunbond web. The body side liner was a 0.75 ounce per square yard (25.4 gsm) polypropylene spunbond web having an average fiber size of three denier.

The body side liner was treated with 0.3 percent by weight, based upon the total weight of the liner, Triton X-102 surfactant which at least partially coated the spunbond fibers. Triton X-102 surfactant is a octylphenoxypolyethoxyethanol nonionic surfactant which is available from the Union Carbide Chemicals and Plastics Company, Inc. of Danbury, Conn. The absorbent core for the training pant had a total weight of 28 grams (one ounce) with 16 grams (0.56 ounces) of Kimberly-Clark CR-254 wood pulp fluff and 12 grams (0.42 ounces) of SAB 836 cross-linked polyacrylate particulate superabsorbent from Stockhausen in Greensboro, N.C. The wood pulp fluff and superabsorbent particles were mixed together to form the absorbent core and the core was wrapped with a 9.79 pound per ream non-optically brightened wet strength tissue wrap sheet. The training pant also contained elastic side panels, inboard containment flaps and an elastic waist. The top sheet or body side liner was attached to the wrap sheet of the absorbent core using spray adhesive. Such training pants are further explained in U.S. Pat. No. 4,940,464 to Van Gompel et al. which is incorporated herein by reference in its entirety.

The training pant according to the present invention was made in the same fashion as the above-described Kimberly-Clark Huggies® Pull-ups® training pant except that the basis weight of the spunbond polypropylene body side liner was reduced in basis weight from 0.75 ounces per square yard (osy) (25.4 gsm) to 0.6 osy (20.3 gsm). The average fiber size for the spunbond fibers was 2.5 denier. In addition, instead of using the Triton X-102 surfactant, the body side liner was treated with 3 percent by weight, based upon the total weight of the liner, of an aqueous dispersion of Ahcovel® Base N-62 liquid nonionic textile softener from ICI Americas, Inc. of Wilmington, Del. Ahcovel® textile softener is a blend of sorbitan monooleate (CAS 1338-43-8) and polyethoxylated hydrogenated castor oil (CAS 61788-85-0). The Ahcovel® N-62 textile softener at least partially coated the spunbond fibers.

All three products were tested with the side panels removed and the elastics cut to permit the products to lay as flat as possible for testing. Each of the three products were separately insulted with 80 milliliters of room temperature (72° to 74° F.) (22° to 23° C.) 0.9 percent saline solution and tested in accordance with the relative surface moisture test procedure and equipment described above. The relative surface moisture values (Table II) were calculated from the raw values on the chart recorder set forth in Table I below. Two samples each of the present invention and the other products were run and the values were averaged and then plotted in graph form in FIG. 2 of the drawings. The data points and curve for the relative surface moisture values for the current Kimberly-Clark Huggies® Pull-ups® training pants ("Pant 1") were plotted using "plus signs" ("+") while the data points and curve for the Procter and Gamble training pants ("K-C Pant") were plotted using "squares." The data points for the present invention ("Invention") were plotted using "diamonds." Values were recorded over a period of ten minutes. From the curve, values were calculated at twelve second intervals.

TABLE I

Raw Surface Moisture Data

| Minutes | Invention | | Pant 1 | | K-C Pant | |
|---|---|---|---|---|---|---|
| | Sample 1 | Sample 2 | Sample 1 | Sample 2 | Sample 1 | Sample 2 |
| 0.0 | 80.0 | 75.0 | 81.5 | 82.0 | 80.0 | 79.0 |
| 0.2 | 80.0 | 75.5 | 81.5 | 82.5 | 80.5 | 79.0 |
| 0.4 | 79.5 | 75.0 | 81.5 | 82.5 | 73.0 | 71.0 |
| 0.6 | 77.0 | 74.0 | 81.5 | 82.5 | 60.0 | 60.0 |
| 0.8 | 75.0 | 71.5 | 81.0 | 82.0 | 55.0 | 54.0 |
| 1.0 | 72.0 | 69.0 | 81.0 | 82.0 | 52.0 | 51.0 |
| 1.2 | 70.0 | 67.0 | 80.5 | 81.0 | 50.5 | 49.0 |
| 1.4 | 68.5 | 65.5 | 78.0 | 80.0 | 49.0 | 47.5 |
| 1.6 | 67.0 | 64.5 | 76.0 | 78.0 | 47.5 | 46.5 |
| 1.8 | 66.0 | 63.0 | 74.0 | 77.0 | 46.5 | 45.0 |
| 2.0 | 64.5 | 62.0 | 73.0 | 76.5 | 46.0 | 44.5 |
| 2.2 | 63.0 | 61.5 | 71.0 | 76.0 | 45.0 | 43.5 |
| 2.4 | 62.5 | 61.0 | 70.5 | 75.0 | 44.5 | 43.0 |
| 2.6 | 61.5 | 60.0 | 70.0 | 74.5 | 44.0 | 42.5 |
| 2.8 | 60.5 | 59.0 | 70.0 | 74.0 | 43.5 | 42.5 |
| 3.0 | 59.5 | 58.0 | 69.5 | 73.5 | 43.5 | 42.5 |
| 3.2 | 59.0 | 57.5 | 69.0 | 73.0 | 43.0 | 42.0 |
| 3.4 | 58.0 | 57.5 | 68.5 | 72.5 | 43.0 | 42.0 |
| 3.6 | 57.5 | 57.0 | 68.0 | 72.0 | 43.0 | 41.5 |
| 3.8 | 57.0 | 56.5 | 67.5 | 71.5 | 42.5 | 41.5 |
| 4.0 | 56.5 | 56.0 | 67.5 | 71.5 | 42.5 | 41.5 |
| 4.2 | 56.0 | 55.5 | 67.0 | 71.0 | 42.5 | 41.0 |
| 4.4 | 55.5 | 55.5 | 67.0 | 71.0 | 42.0 | 41.0 |
| 4.6 | 55.0 | 55.0 | 66.5 | 70.5 | 42.0 | 41.0 |
| 4.8 | 54.5 | 55.0 | 66.5 | 70.0 | 42.0 | 41.0 |
| 5.0 | 54.0 | 54.5 | 66.0 | 70.0 | 42.0 | 40.5 |
| 5.2 | 53.5 | 54.5 | 67.6 | 70.0 | 42.0 | 40.5 |
| 5.4 | 53.0 | 54.0 | 67.6 | 70.0 | 42.0 | 40.5 |
| 5.6 | 52.5 | 54.0 | 67.6 | 69.5 | 41.5 | 40.5 |
| 5.8 | 52.0 | 53.5 | 66.9 | 69.5 | 41.5 | 40.5 |
| 6.0 | 52.0 | 53.5 | 66.9 | 69.5 | 41.5 | 40.5 |
| 6.2 | 52.0 | 53.0 | 66.9 | 69.5 | 41.5 | 40.5 |
| 6.4 | 51.5 | 53.0 | 66.2 | 69.0 | 41.5 | 40.5 |
| 6.6 | 51.5 | 52.5 | 66.2 | 69.0 | 41.0 | 40.5 |
| 6.8 | 51.0 | 52.5 | 66.2 | 69.0 | 41.0 | 40.5 |
| 7.0 | 51.0 | 52.0 | 66.2 | 69.0 | 41.0 | 40.5 |
| 7.2 | 51.0 | 52.0 | 65.4 | 69.0 | 41.0 | 40.5 |
| 7.4 | 51.0 | 52.0 | 65.4 | 68.5 | 41.0 | 40.5 |
| 7.6 | 51.0 | 51.5 | 64.7 | 68.5 | 41.5 | 40.5 |
| 7.8 | 50.5 | 51.5 | 64.7 | 68.5 | 41.5 | 40.5 |
| 8.0 | 50.5 | 51.5 | 64.0 | 68.5 | 41.5 | 41.0 |
| 8.2 | 50.0 | 51.5 | 64.0 | 68.0 | 41.5 | 41.0 |
| 8.4 | 50.0 | 51.0 | 63.2 | 68.0 | 41.5 | 41.0 |
| 8.6 | 50.0 | 51.0 | 63.2 | 68.0 | 41.5 | 41.0 |

TABLE I-continued

Raw Surface Moisture Data

| | Invention | | Pant 1 | | K-C Pant | |
|---|---|---|---|---|---|---|
| Minutes | Sample 1 | Sample 2 | Sample 1 | Sample 2 | Sample 1 | Sample 2 |
| 8.8 | 49.5 | 51.0 | 63.2 | 68.0 | 41.5 | 41.0 |
| 9.0 | 49.5 | 51.0 | 63.2 | 67.5 | 41.5 | 41.0 |
| 9.2 | 49.5 | 51.0 | 63.2 | 67.5 | 41.5 | 41.0 |
| 9.4 | 49.5 | 51.0 | 62.5 | 67.0 | 41.5 | 41.0 |
| 9.6 | 49.5 | 51.0 | 62.5 | 67.0 | 41.5 | 41.0 |
| 9.8 | 49.0 | 51.0 | 62.5 | 67.0 | 41.5 | 41.0 |
| 10.0 | 49.0 | 51.0 | 62.5 | 67.0 | 41.5 | 41.0 |
| Saturated Value | 82.0 | 82.0 | 88.0 | 88.0 | 83.5 | 83.5 |

TABLE II

Relative Surface Moisture (percentage)

| | Invention | | Pant 1 | | K-C Pant | | Averages | | |
|---|---|---|---|---|---|---|---|---|---|
| Minutes | Sample 1 | Sample 2 | Sample 1 | Sample 2 | Sample 1 | Sample 2 | Invention | Pant 1 | K-C Pant |
| 0.0 | 96.8 | 88.7 | 90.4 | 91.2 | 94.5 | 92.9 | 92.7 | 90.8 | 93.7 |
| 0.2 | 96.8 | 89.5 | 90.4 | 91.9 | 95.3 | 92.9 | 93.1 | 91.2 | 94.1 |
| 0.4 | 96.0 | 88.7 | 90.4 | 91.9 | 83.5 | 80.3 | 92.3 | 91.2 | 81.9 |
| 0.6 | 91.9 | 87.1 | 90.4 | 91.9 | 63.0 | 63.0 | 89.5 | 91.2 | 63.0 |
| 0.8 | 88.7 | 83.1 | 89.7 | 91.2 | 55.1 | 53.5 | 85.9 | 90.4 | 54.3 |
| 1.0 | 83.9 | 79.0 | 89.7 | 91.2 | 50.4 | 48.8 | 81.5 | 90.4 | 49.6 |
| 1.2 | 80.6 | 75.8 | 89.0 | 89.7 | 48.0 | 45.7 | 78.2 | 89.3 | 46.9 |
| 1.4 | 78.2 | 73.4 | 85.3 | 88.2 | 45.7 | 43.3 | 75.8 | 86.8 | 44.5 |
| 1.6 | 75.8 | 71.8 | 82.4 | 85.3 | 43.3 | 41.7 | 73.8 | 83.8 | 42.5 |
| 1.8 | 74.2 | 69.4 | 79.4 | 83.8 | 41.7 | 39.4 | 71.8 | 81.6 | 40.6 |
| 2.0 | 71.8 | 67.7 | 77.9 | 83.1 | 40.9 | 38.6 | 69.8 | 80.5 | 39.8 |
| 2.2 | 69.4 | 66.9 | 75.0 | 82.4 | 39.4 | 37.0 | 68.1 | 78.7 | 38.2 |
| 2.4 | 68.5 | 66.1 | 74.3 | 80.9 | 38.6 | 36.2 | 67.3 | 77.6 | 37.4 |
| 2.6 | 66.9 | 64.5 | 73.5 | 80.1 | 37.8 | 35.4 | 65.7 | 76.8 | 36.6 |
| 2.8 | 65.3 | 62.9 | 73.5 | 79.4 | 37.0 | 35.4 | 64.1 | 76.5 | 36.2 |
| 3.0 | 63.7 | 61.3 | 72.8 | 78.7 | 37.0 | 35.4 | 62.5 | 75.7 | 36.2 |
| 3.2 | 62.9 | 60.5 | 72.1 | 77.9 | 36.2 | 34.6 | 61.7 | 75.0 | 35.4 |
| 3.4 | 61.3 | 60.5 | 71.3 | 77.2 | 36.2 | 34.6 | 60.9 | 74.3 | 35.4 |
| 3.6 | 60.5 | 59.7 | 70.6 | 76.5 | 36.2 | 33.9 | 60.1 | 73.5 | 35.0 |
| 3.8 | 59.7 | 58.9 | 69.9 | 75.7 | 35.4 | 33.9 | 59.3 | 72.8 | 34.6 |
| 4.0 | 58.9 | 58.1 | 69.9 | 75.7 | 35.4 | 33.9 | 58.5 | 72.8 | 34.6 |
| 4.2 | 58.1 | 57.3 | 69.1 | 75.0 | 35.4 | 33.1 | 57.7 | 72.1 | 34.3 |
| 4.4 | 57.3 | 57.3 | 69.1 | 75.0 | 34.6 | 33.1 | 57.3 | 72.1 | 33.9 |
| 4.6 | 56.5 | 56.5 | 68.4 | 74.3 | 34.6 | 33.1 | 56.5 | 71.3 | 33.9 |
| 4.8 | 55.6 | 56.5 | 68.4 | 73.5 | 34.6 | 33.1 | 56.0 | 71.0 | 33.9 |
| 5.0 | 54.8 | 55.6 | 67.6 | 73.5 | 34.6 | 32.3 | 55.2 | 70.6 | 33.5 |
| 5.2 | 54.0 | 55.6 | 67.6 | 73.5 | 34.6 | 32.3 | 54.8 | 70.6 | 33.5 |
| 5.4 | 53.2 | 54.8 | 67.6 | 73.5 | 34.6 | 32.3 | 54.0 | 70.6 | 33.5 |
| 5.6 | 52.4 | 54.8 | 67.6 | 72.8 | 33.9 | 32.3 | 53.6 | 70.2 | 33.1 |
| 5.8 | 51.6 | 54.0 | 66.9 | 72.8 | 33.9 | 32.3 | 52.8 | 69.9 | 33.1 |
| 6.0 | 51.6 | 54.0 | 66.9 | 72.8 | 33.9 | 32.3 | 52.8 | 69.9 | 33.1 |
| 6.2 | 51.6 | 53.2 | 66.9 | 72.8 | 33.9 | 32.3 | 52.4 | 69.9 | 33.1 |
| 6.4 | 50.8 | 53.2 | 66.2 | 72.1 | 33.9 | 32.3 | 52.0 | 69.1 | 33.1 |
| 6.6 | 50.8 | 52.4 | 66.2 | 72.1 | 33.1 | 32.3 | 51.6 | 69.1 | 32.7 |
| 6.8 | 50.0 | 52.4 | 66.2 | 72.1 | 33.1 | 32.3 | 51.2 | 69.1 | 32.7 |
| 7.0 | 50.0 | 51.6 | 66.2 | 72.1 | 33.1 | 32.3 | 50.8 | 69.1 | 32.7 |
| 7.2 | 50.0 | 51.6 | 65.4 | 72.1 | 33.1 | 32.3 | 50.8 | 68.8 | 32.7 |
| 7.4 | 50.0 | 51.6 | 65.4 | 71.3 | 33.1 | 32.3 | 50.8 | 68.4 | 32.7 |
| 7.6 | 50.0 | 50.8 | 64.7 | 71.3 | 33.9 | 32.3 | 50.4 | 68.0 | 33.1 |
| 7.8 | 49.2 | 50.8 | 64.7 | 71.3 | 33.9 | 32.3 | 50.0 | 68.0 | 33.1 |
| 8.0 | 49.2 | 50.8 | 64.0 | 71.3 | 33.9 | 33.1 | 50.0 | 67.6 | 33.5 |
| 8.2 | 48.4 | 50.8 | 64.0 | 70.6 | 33.9 | 33.1 | 49.6 | 67.3 | 33.5 |
| 8.4 | 48.4 | 50.0 | 63.2 | 70.6 | 33.9 | 33.1 | 49.2 | 66.9 | 33.5 |
| 8.6 | 48.4 | 50.0 | 63.2 | 70.6 | 33.1 | 33.1 | 49.2 | 66.9 | 33.5 |
| 8.8 | 47.6 | 50.0 | 63.2 | 70.6 | 33.9 | 33.1 | 48.8 | 66.9 | 33.5 |
| 9.0 | 47.6 | 50.0 | 63.2 | 69.9 | 33.9 | 33.1 | 48.8 | 66.5 | 33.5 |
| 9.2 | 47.6 | 50.0 | 63.2 | 69.9 | 33.9 | 33.1 | 48.8 | 66.5 | 33.5 |
| 9.4 | 47.6 | 50.0 | 62.5 | 69.1 | 33.9 | 33.1 | 48.8 | 65.8 | 33.5 |
| 9.6 | 47.6 | 50.0 | 62.5 | 69.1 | 33.9 | 33.1 | 48.8 | 65.8 | 33.5 |
| 9.8 | 46.8 | 50.0 | 62.5 | 69.1 | 33.9 | 33.1 | 48.4 | 65.8 | 33.5 |
| 10.0 | 46.8 | 50.0 | 62.5 | 69.1 | 33.9 | 33.1 | 48.4 | 65.8 | 33.5 |

Figure 2:
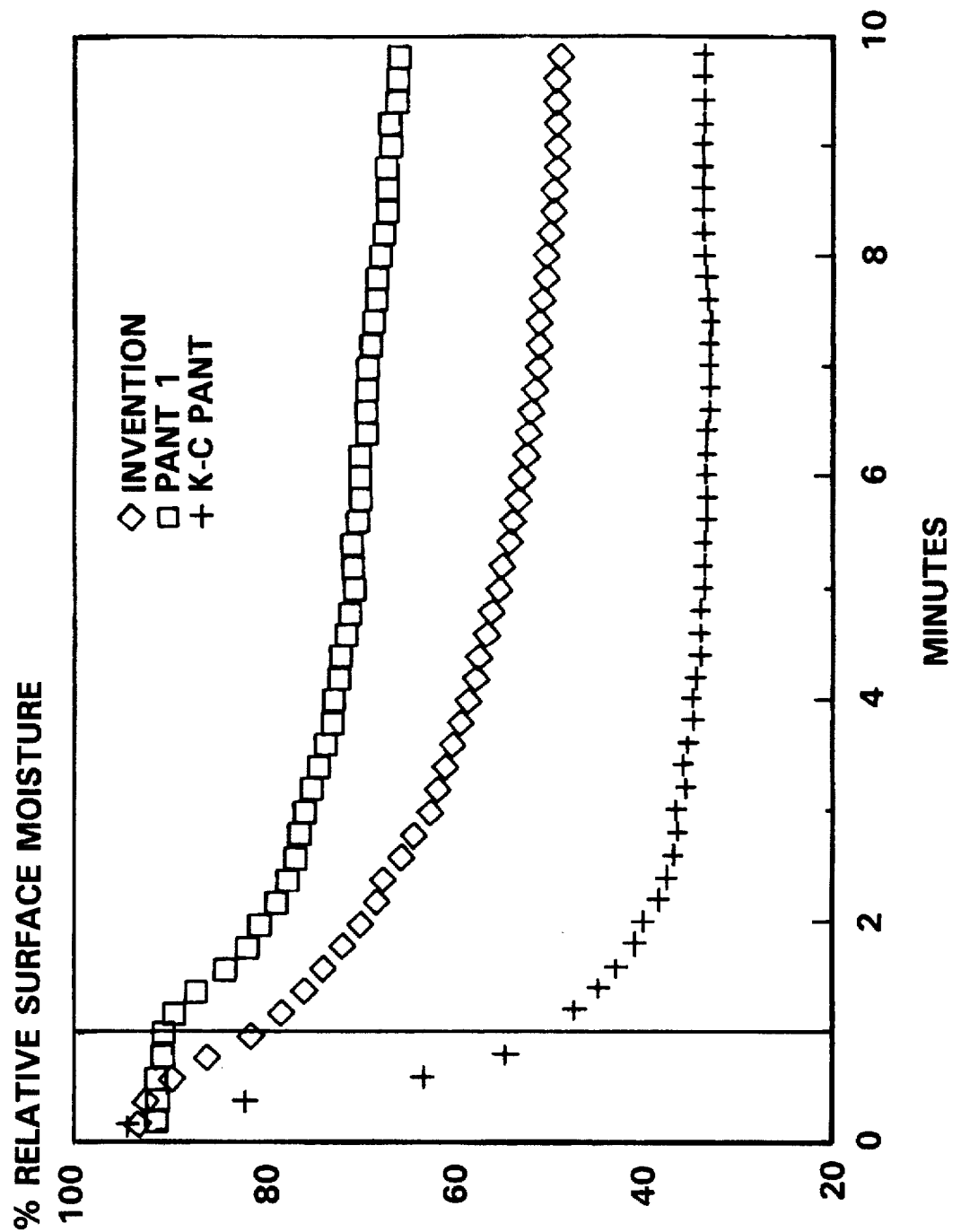
FIG. 2 is a graph showing relative surface moisture values over time for several personal care absorbent products including the present invention.

Turning to the graph in FIG. 2, it can be seen that the Procter and Gamble training pant had an approximate 90 percent initial relative surface moisture. This value was maintained through the first minute and then between one and three minutes the value dropped to approximately 75 percent. Within the next seven minutes the percent moisture began to flatten out to a value of 65 percent at the end of ten minutes. Thus this product started out wet and continued to stay wet. In contrast, the currently available Kimberly-Clark Huggies® Pull-ups® training pants started off very wet at almost 94 percent relative surface moisture but then dropped off to a value of 50 percent by the end of one minute. By ten minutes the relative surface moisture had dropped to a low of 35 percent. Thus, this training pant dried out more quickly after being insulted with the saline solution.

The training pants according to the present invention showed a balance between the other two products. As can be seen from the graph in FIG. 2, the curve for the present invention fell between the other two curves. By using the Ahcovel® wetness indicator treatment on the liner material, the values on the curve were maintained at a much higher level than the current Kimberly-Clark training pant during the first several minutes and the values then dropped down to a more acceptable level by the end of ten minutes. At one minute, the training pant according to the present invention had a relative surface moisture value of approximately 80 percent. However, by ten minutes the value had dropped to approximately 50 percent.

Thus, it can be seen that the present invention provides a personal care absorbent product which maintains a high relative surface wetness for at least one minute and then, within a very short period of time, approximately ten minutes, has a relative surface moisture value that drops to approximately 50 percent thus creating a product which has a dry feel that is more comfortable to wear until such time as it is possible or convenient to change the soiled product. Consequently, the present invention has practical application with respect to all types of personal care absorbent products.

Having thus described the invention in detail, it should be apparent that various modifications and changes can be made in the present invention without departure from the spirit and scope of the following claims.

We claim:

1. A personal care absorbent article comprising a liquid permeable body side liner, an outer cover and an absorbent core disposed between said body side liner and said outer cover to form said article, said body side liner being sealed to said outer cover to encapsulate said absorbent core and comprising a nonwoven web having a plurality of fibers, said web including a wetness indicator treatment comprising a mixture of sorbitan monooleate and polyethoxylated hydrogenated castor oil, said article having a relative surface moisture value of 60 percent or greater at approximately 1 minute and a relative surface moisture value of 55 percent or less at approximately 10 minutes.

2. The personal care absorbent article of claim 1 wherein said wetness indicator treatment is present on said web in an add-on of from one to five percent by weight based upon the total weight of said web.

3. The personal care absorbent article of claim 1 wherein said article is in the form of a training pant.

4. The personal care absorbent product of claim 1 wherein said article is in the form of a diaper.

5. The personal care absorbent article of claim 1 wherein said article is in the form of an incontinence garment.

6. A personal care absorbent article comprising:

a liquid permeable body side liner, an outer cover, and an absorbent core disposed between said body side liner and said outer cover, said body side liner being sealed to said outer cover to encapsulate said absorbent core, said body side liner comprising a fibrous polyolefin nonwoven web having a basis weight ranging between about 0.5 and about 0.85 ounces per square yard, said web having a wetness indicator treatment comprising a mixture of sorbitan monooleate and polyethoxylated hydrogenated castor oil, said outer cover comprising a layer of polyolefin film attached to a layer of fibrous nonwoven web, said absorbent core containing at least 20 percent by weight superabsorbent based upon the total weight of said absorbent core, said article having a relative surface moisture value of 60 percent or greater at approximately one minute and a relative surface moisture value of 55 percent or less at approximately ten minutes.

7. The personal care absorbent article of claim 6 wherein said article is in the form of a training pant.

8. The personal care absorbent article of claim 6 wherein said article is in the form of a diaper.

9. The personal care absorbent article of claim 6 wherein said article is in the form of an incontinence garment.

\* \* \* \* \*

UNITED STATES PATENT AND TRADEMARK OFFICE
CERTIFICATION OF CORRECTION

PATENT NO. : 5,702,377

DATED : December 30, 1997

INVENTOR(S): Collier, IV et al.

It is certified that an error appears in the above-identified patent and that said Letters Patent is hereby corrected as shown below:

Column 4, line 65, "such things fluid" should read --such things as fluid--.

Signed and Sealed this

Twenty-fifth Day of August, 1998

Attest:

BRUCE LEHMAN

Attesting Officer      Commissioner of Patents and Trademarks